United States Patent
Hardegree

(10) Patent No.: US 8,690,850 B2
(45) Date of Patent: Apr. 8, 2014

(54) STITCH BONDED FABRIC WITH DIRECTIONAL STRETCH CHARACTER AND DIAPER FORMED THEREFROM

(75) Inventor: Michelis Hardegree, Columbus, NC (US)

(73) Assignee: Tietex International, Ltd., Spartanburg, SC (US)

( * ) Notice: Subject to any disclaimer, the term of this patent is extended or adjusted under 35 U.S.C. 154(b) by 521 days.

(21) Appl. No.: 12/552,902

(22) Filed: Sep. 2, 2009

(65) Prior Publication Data

US 2010/0057032 A1  Mar. 4, 2010

Related U.S. Application Data

(60) Provisional application No. 61/093,516, filed on Sep. 2, 2008.

(51) Int. Cl.
  A61F 13/15  (2006.01)
  A61F 13/20  (2006.01)

(52) U.S. Cl.
  USPC ............ 604/385.24; 604/385.25; 604/385.29; 604/385.3

(58) Field of Classification Search
  USPC ............ 604/385.27, 385.24, 385.25, 385.26, 604/385.28, 385.29, 385.3; 2/220, 221, 2/222, 236, 237, 275, 404, 407
  See application file for complete search history.

(56) References Cited

U.S. PATENT DOCUMENTS

| | | | |
|---|---|---|---|
| 3,664,336 A | | 5/1972 | Gelston |
| 3,717,150 A | * | 2/1973 | Schwartz ..................... 604/372 |
| 4,861,652 A | | 8/1989 | Lippert |
| 4,931,343 A | | 6/1990 | Becker et al. |
| 5,192,600 A | * | 3/1993 | Pontrelli et al. ............. 428/102 |
| 5,203,186 A | * | 4/1993 | Zafiroglu ........................ 66/192 |
| 5,826,905 A | * | 10/1998 | Tochacek et al. ......... 280/743.1 |
| 5,916,207 A | | 6/1999 | Toyoda et al. |
| 6,419,667 B1 | | 7/2002 | Avalon et al. |
| 6,855,392 B2 | | 2/2005 | Wildeman et al. |
| 6,869,660 B2 | | 3/2005 | Wildeman |
| 7,294,387 B2 | | 11/2007 | Wildeman |
| 2003/0056703 A1 | | 3/2003 | Blake |
| 2003/0077970 A1 | | 4/2003 | Delucia |
| 2003/0109844 A1 | * | 6/2003 | Gibbs .......................... 604/389 |
| 2008/0280094 A1 | | 11/2008 | Wildeman et al. |

* cited by examiner

*Primary Examiner* — Jackie Ho
*Assistant Examiner* — Peter S Vasat
(74) *Attorney, Agent, or Firm* — J.M. Robertson, LLC

(57) ABSTRACT

A diaper wherein at least one of the waist band, side panels, leg cuffs and fastening system landing zone includes a textile material of stitch bonded construction. The textile material includes selectively applied zones of stitches formed from elastomeric yarns with adjacent zones having stitches formed from inelastic yarns. The textile material provides stretch of a desired degree in the cross-machine direction while maintaining substantial dimensional stability in the machine direction.

14 Claims, 4 Drawing Sheets

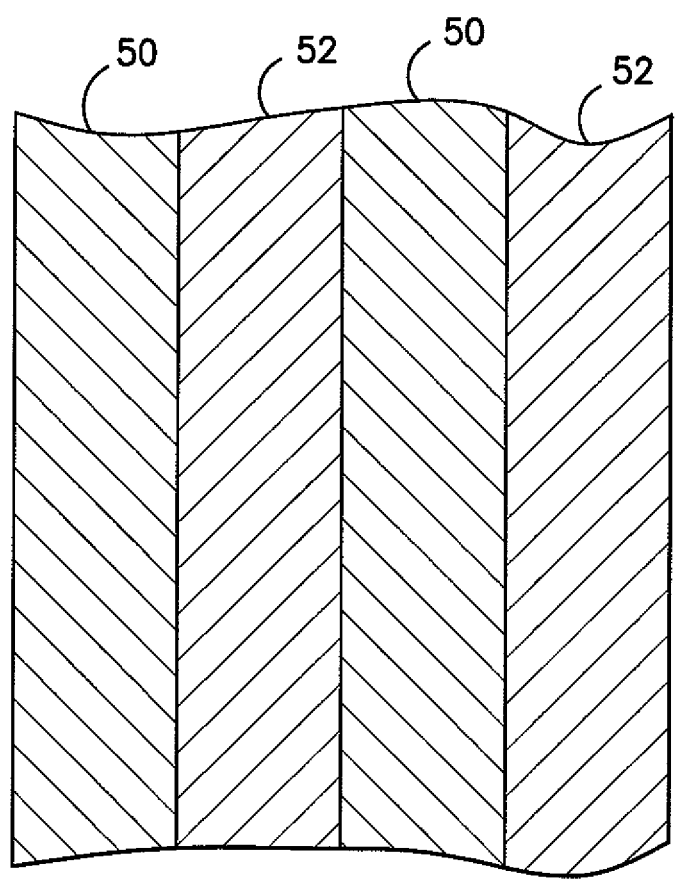
FIG. -2-

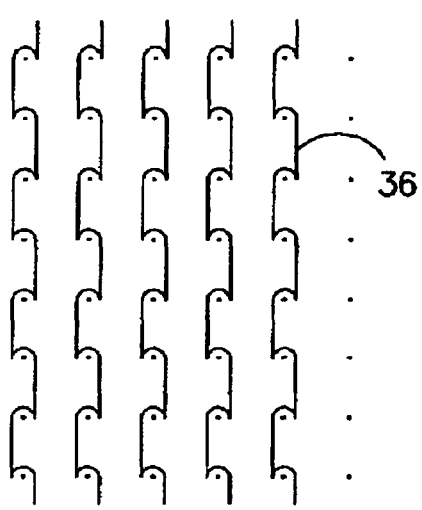
FIG. -3-
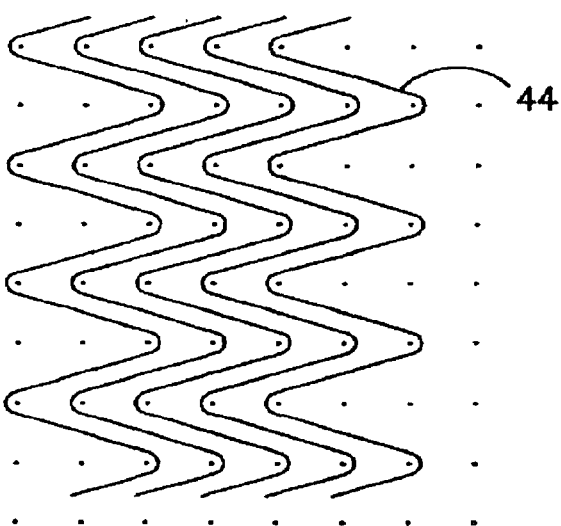
FIG. -4-

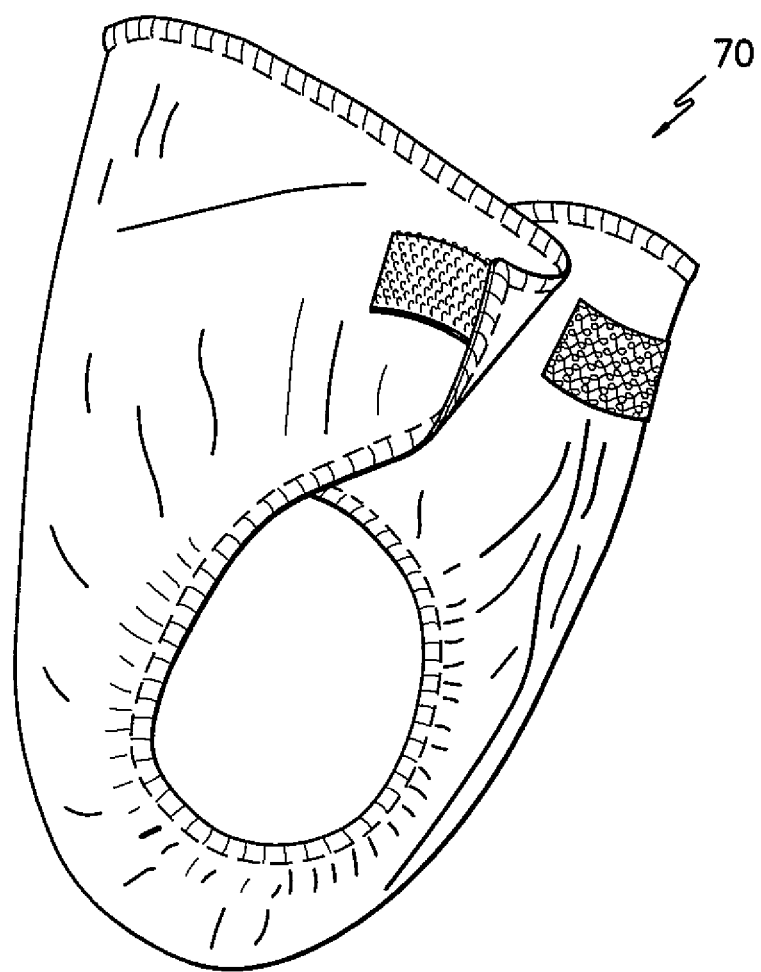
FIG. —5—

STITCH BONDED FABRIC WITH DIRECTIONAL STRETCH CHARACTER AND DIAPER FORMED THEREFROM

CROSS-REFERENCE TO RELATED APPLICATIONS

This application claims the benefit of and priority from U.S. provisional application No. 61/093,516 in the name of Hardegree filed Sep. 2, 2008, the contents of which are incorporated herein in their entirety.

TECHNICAL FIELD

The present invention relates generally to diapers, and more particularly, to the use of stitch bonded fabrics of elastomeric character in diaper construction. In particular, the present invention relates to stretchable portions of diapers incorporating fabrics of stitch bonded construction incorporating at least a first stitch zone incorporating stitches formed from a first group of yarns of substantially inelastic character in substantially adjacent relation to at least a second stitch zone incorporating stitches formed from at least a second group of elastomeric yarns. The first stitch zone and the second stitch zone are disposed at predefined positions along the cross-machine direction of the fabric.

BACKGROUND OF THE INVENTION

In recent years, snug fit has been a focus for diaper manufacturers seeking to improve the containment of urinary and bowel release. In accordance with this effort, stretch features have been incorporated into various areas of the diapers including leg cuffs, waist bands, side panels and closure system landing zones. According to one practice, such stretch features have been achieved by gluing cut stands of an elastomeric yarn such as SPANDEX® or the like in sandwiched relation between two layers of a nonwoven fabric. According to another practice, a stretchable polymeric film is sandwiched between layers of nonwoven. While these practices may provide a level of benefit, they require two layers of nonwoven material. Moreover, it may be difficult to achieve controlled and repeatable extension and retraction.

SUMMARY OF THE INVENTION

The present invention provides advantages and alternatives over the prior art by providing a diaper incorporating stretch elements formed from a textile sheet element of stitch bonded construction having selectively applied zones of stitches formed from elastomeric yarns with adjacent zones having stitches formed from yarns of inelastic character to provide stretch of a desired degree in the cross-machine direction while maintaining substantial dimensional stability in the machine direction of the fabric.

BRIEF DESCRIPTION OF THE DRAWINGS

The accompanying drawings which are incorporated in and which constitute a part of this specification illustrate several exemplary constructions and procedures in accordance with the present invention and, together with the general description of the invention given above and the detailed description set forth below, serve to explain the principles of the invention wherein:

FIG. 2 illustrates schematically the fabric having adjacent zones of high stretch and low stretch character.

FIG. 3 illustrates schematically an exemplary stitch pattern for zones of low stretch character.

FIG. 4 illustrates schematically an exemplary stitch pattern for zones of high stretch character.

FIG. 5 illustrates an exemplary diaper incorporating various stretch zones.

Figure 1:
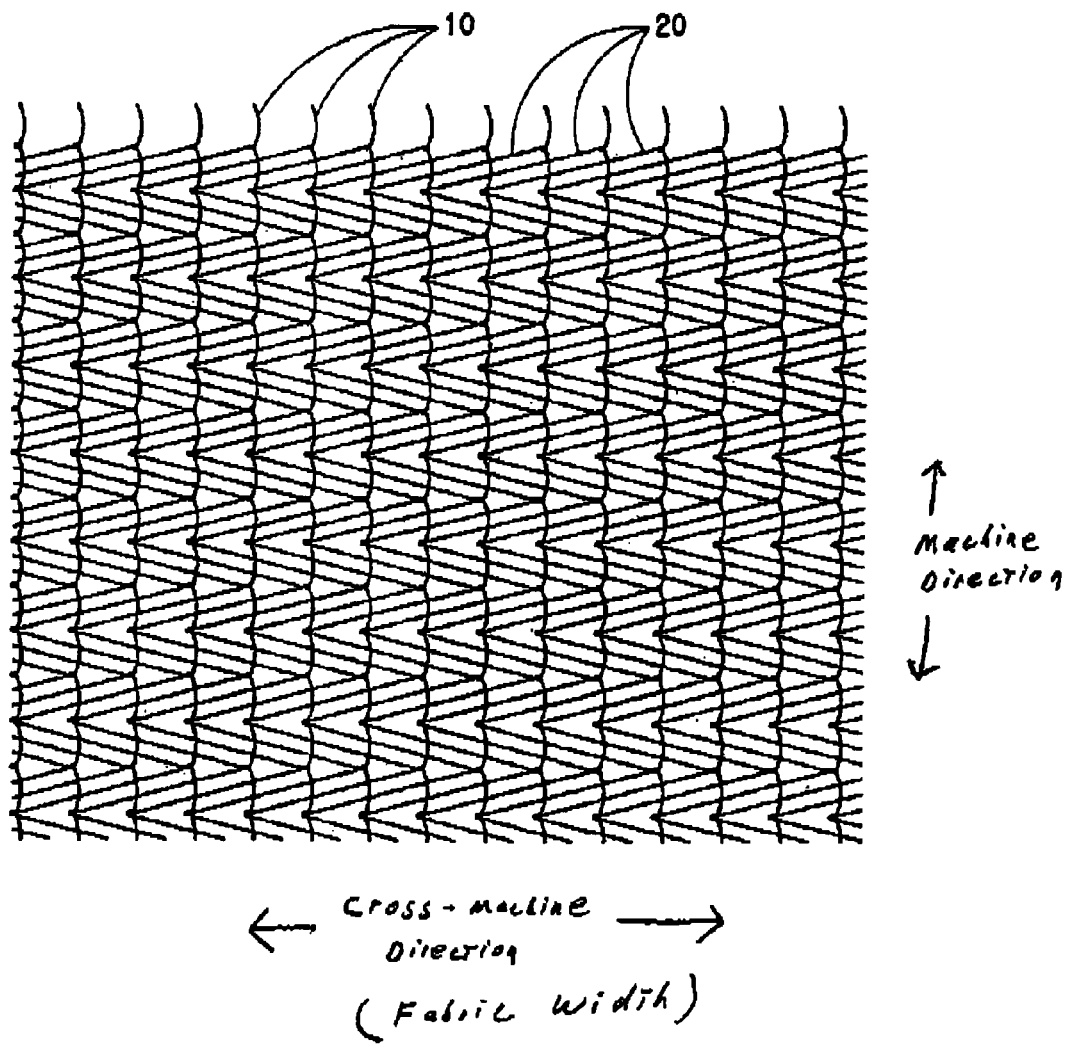
FIG. 1 illustrates schematically a two bar stitch bonding process for selectively forming a patterned yarn system of elastomeric and inelastic yarns through a fibrous substrate.

While the invention has been illustrated and will hereinafter be described in connection with certain exemplary embodiments and practices, it is to be understood that in no event is the invention to be limited to such illustrated and described embodiments and practices. On the contrary, it is intended that the present invention shall extend to all alternatives and modifications as may embrace the general principles of this invention within the full and true spirit and scope thereof.

DESCRIPTION OF THE PREFERRED EMBODIMENTS

The present invention contemplates a diaper incorporating a textile sheet material of stitch bonded construction having selectively applied zones of stitches formed from elastomeric yarns with adjacent zones having stitches formed from inelastic yarns. Such materials may find application in various portions of the diaper including leg cuffs, waist bands, side panels and closure system landing zones.

Fabric formation using so-called stitch bonding techniques is known. In such processes, a multiplicity of stitching yarns is passed repeatedly in stitching relation through a substrate layer in closely spaced rows so as to form a coordinated arrangement of surface stitches in covering relation to the substrate. By way of example only, one method contemplated to form a stitch bonded construction with zones of different stitch character involves the use of a so called two bar stitch bonding procedure shown schematically in FIG. 1. In this practice, a substrate material 30 of nonwoven construction such as a carded and cross-lapped fleece or a needle punched or spun bonded fleece is conveyed to a stitch-forming position in the direction indicated by the arrow. It is also contemplated that the substrate material may be formed from multiple layers if desired. By way of example only, and not limitation, it is contemplated that one layer may be a substantially hydrophobic fibrous material for passage of fluid while an underlying layer may be a substantially hydrophilic material for retention of fluid. It is also contemplated that materials of different pore size may be used. By way of example only, and not limitation, it is contemplated that one layer may have a relatively open structure adequate for particle retention, while another layer may incorporate fine pores to promote absorbency. Of course, any combination of these features may be utilized.

The stitch bonding machine typically incorporates a row of reciprocating needles 34 (only one shown) extending in adjacent relation to one another across the width of the substrate material 30 substantially transverse to the direction of movement of the substrate material 30. The so called gauge or needle density in the cross machine direction may be adjusted as desired. By way of example only, and not limitation, it is contemplated that the needle density may be in the range of about 7 to about 28 needles per inch although higher and lower needle densities may likewise be used if desired.

According to one contemplated practice, two yarn systems (i.e. two bars) are used to form stitches through the substrate material at various zones. A first group of substantially inelastic yarns 36 of low stretchability such as a commodity polyester yarn having a linear density of about 40 to about 150 denier is carried by a first guide 38 for cooperative engagement with predefined groups of the needles 34. Of course, higher or lower denier levels may be used if desired. A second group of elastomeric yarns 44 of high stretchability such as SPANDEX® or the like having a linear density of about 40 to about 1,000 denier is carried by a second guide 46 for cooperative engagement with other groups of the needles 34. In this regard, the term "elastomeric yarn" is defined as a yarn which is stretchable to at least twice its original length by the application of tension followed by a return to its original length under ambient conditions upon the removal of the tensioning force. Inelastic yarns do not satisfy this criteria. For each yarn system, the needles may be fully or partially threaded.

By way of example only, and not limitation, the first group of inelastic yarns 36 of low stretch character may be stitched in a chain stitch notation as shown in FIG. 3 arranged in closely spaced parallel rows along the machine direction. This chain stitch arrangement using low stretch yarns provides zones 50 (FIG. 2) of substantial biaxial stability. Of course, other stitching arrangements may be used if desired. The second group of elastomeric yarns 44 may be stitched with a notation such that the yarn elements are arranged along lines substantially in the cross machine direction, although a chain stitch or other substantially straight line stitch arrangement may also be used. By way of example only, and not limitation, one potentially desirable stitch arrangement for the elastomeric yarns is shown in FIG. 4. In the illustrated exemplary arrangement each yarn is shifted laterally by two needles between stitches. This orients the yarns substantially in the cross machine direction within high stretch zones 52 (FIG. 2) and provides substantial stretch in the cross-machine direction without substantially increasing the stretch in the machine direction. While a lateral shift of two needles between stitches is illustrated, it is likewise contemplated that a shift of one needle or three or more needles also may be used if desired. In the event that a chain stitch or other straight line stitch without needle shifting is used, some stretch in the cross-machine direction will still be possible due to the elastomeric character of the yarns.

The use of stitch bonding technology to insert elastomeric yarns into a non-woven substrate only in discreet locations, zones or channels provides excellent performance and cost efficiency. In addition, the use of the stitch bonding procedure eliminates the need for two non-woven layers sandwiching elastomeric yarns or film. Moreover, the use of covered elastomeric yarns permits the formation of a face surface of soft feel suitable for contacting the skin of a user. Further, the directional stretch may be achieved using a common substrate for the high stretch and low stretch zones.

Providing substantial stretch in the cross machine direction while maintaining relatively low stretch in the machine direction may facilitate subsequent processing during diaper formation. Specifically such low stretch in the machine direction permits rolls of the formed fabric to be readily processed in high tension diaper manufacturing lines without necking down or wrinkling beyond an acceptable level. The zones of biaxial dimensional stability may also aid in joining a component such as a waist band 60, side panel 62, leg cuff 64, fastening system landing zone 66 or the like to adjacent portions of a diaper 70 by gluing, ultrasonic welding or other joining techniques. In addition, by using stitch bonding, a wide base fabric may be formed with a pattern of adjacent zones of high stretch and low stretch character across the width. This permits the base fabric to be slit to multiple smaller widths having the desired characteristics prior to being used for diaper production.

The present invention has now been described with reference to several embodiments thereof. However, it will be apparent to those skilled in the art that many changes can be made in the embodiments described without departing from the scope of the present invention. Thus, in no event is the scope of the present invention to be limited to the structures and practices described in this application. Rather, it is intended that the invention shall extend to all alternatives and equivalents embracing the broad principles of this invention within the fill spirit and scope thereof.

What is claimed is:

1. A diaper comprising:
    a waist band, side panels, leg cuffs and a hook and loop fastening system landing zone, wherein at least one of the waist band, side panels, leg cuffs and landing zone includes a textile material having at least one localized discreet zone of stretchable character, the textile material having a machine direction and a cross machine direction and including;
    a substrate layer having a width;
    a first plurality of inelastic yarns disposed in a first pattern of stitches through the substrate layer to define at least a first localized defined stitch zone extending partially across the width of the substrate layer, the first localized defined stitch zone comprising a plurality of substantially parallel side by side stitch lines formed by the first plurality of inelastic yarns and running along the machine direction of the textile material, wherein a multiplicity of the side by side stitch lines are disposed in substantially parallel spaced relation to one another across the width of the first localized defined stitch zone; and
    a second plurality of elastomeric yarns disposed in a second pattern of stitches through the substrate layer to define at least a second localized defined stitch zone in adjacent, discreet relation to the first localized defined stitch zone, the second localized defined stitch zone comprising a plurality of zigzag stitch lines formed by the second plurality of elastomeric yarns, wherein a multiplicity of zigzag stitch lines are disposed in adjacent spaced relation to one another across the width of the second localized defined stitch zone, the second localized defined stitch zone characterized by increased stretch in the cross machine direction relative to the first localized defined stitch zone.

2. The diaper as recited in claim 1, wherein the second plurality of elastomeric yarns are covered elastomeric yarns.

3. The diaper as recited in claim 2, wherein the first pattern of stitches is a straight chain stitch and the second pattern of stitches is a substantially zigzag pattern having a lateral yarn shift of one or more needles between stitches.

4. The diaper as recited in claim 1, wherein the first plurality of inelastic yarns are polyester yarns.

5. The diaper as recited in claim 4, wherein the first plurality of inelastic yarns has a linear density of about 40 to about 150 denier.

6. The diaper as recited in claim 1, wherein the second plurality of elastomeric yarns has a linear density of about 40 to about 1000 denier.

7. The diaper as recited in claim 1, wherein the substrate layer is a nonwoven fleece.

8. A diaper comprising:

a waist band, side panels, leg cuffs and a hook and loop fastening system landing zone, wherein at least one of the waist band, side panels, leg cuffs and landing zone includes a textile material having a plurality of localized discreet zones of stretchable character, the textile material having a machine direction and a cross machine direction and including:

a substrate layer having a width;

a first plurality of inelastic yarns disposed in a first pattern of stitches through the substrate layer to define a first plurality of localized defined stitch zones, each extending partially across the width of the substrate layer, the first plurality of localized defined stitch zones each comprising a plurality of substantially parallel side by side stitch lines formed by the first plurality of inelastic yarns and running along the machine direction of the textile material, wherein a multiplicity of the side by side stitch lines are disposed in substantially parallel spaced relation to one another across the width of each of the first localized defined stitch zones; and a second plurality of elastomeric yarns disposed in a second pattern of stitches through the substrate layer to define at least a second plurality of localized defined stitch zones, each disposed in adjacent, discreet relation to at least one of the first plurality of localized defined stitch zones, the second localized defined stitch zones each comprising a plurality of zigzag stitch lines formed by the second plurality of elastomeric yarns, wherein a multiplicity of the zigzag stitch lines are disposed in adjacent spaced relation to one another across the width of each of the second localized defined stitch zones, the second plurality of localized defined stitch zones characterized by increased stretch in the cross machine direction relative to the first plurality of localized defined stitch zones, and wherein the first localized defined stitch zones are arranged in alternating relation to the second localized defined stitch zones across the width of the textile material.

9. The diaper as recited in claim 8, wherein the second plurality of elastomeric yarns are covered elastomeric yarns.

10. The diaper as recited in claim 8, wherein the first pattern of stitches is a straight chain stitch and the second pattern of stitches is a substantially zigzag pattern having a lateral yarn shift of one or more needles between stitches.

11. The diaper as recited in claim 8, wherein the first plurality of inelastic yarns are polyester yarns.

12. The diaper as recited in claim 11, wherein the first plurality of inelastic yarns has a linear density of about 40 to about 150 denier.

13. The diaper as recited in claim 8, wherein the second plurality of elastomeric yarns has a linear density of about 40 to about 1000 denier.

14. The diaper as recited in claim 8, wherein the substrate layer is a nonwoven fleece.

* * * * *